United States Patent [19]
Lobodzinski

[11] Patent Number: 5,619,995
[45] Date of Patent: Apr. 15, 1997

[54] MOTION VIDEO TRANSFORMATION SYSTEM AND METHOD

[76] Inventor: Suave M. Lobodzinski, 5560 St. Irmo Walk, Long Beach, Calif. 90803

[21] Appl. No.: 259,789

[22] Filed: Jun. 14, 1994

Related U.S. Application Data

[63] Continuation-in-part of Ser. No. 158,157, Nov. 24, 1993, abandoned, which is a continuation of Ser. No. 791,962, Nov. 12, 1991, abandoned.

[51] Int. Cl.$^6$ ........................................... A61B 5/05
[52] U.S. Cl. ..................... 128/653.1; 128/630; 348/77
[58] Field of Search .................. 128/653.1, 700, 128/630; 364/413.01, 413.14, 413.15, 413.22; 348/77

[56] References Cited

U.S. PATENT DOCUMENTS

| | | | |
|---|---|---|---|
| 4,382,184 | 5/1983 | Wernikoff | 128/653.1 |
| 4,616,319 | 10/1986 | Peters et al. | 364/414 |
| 4,865,043 | 9/1989 | Shimoni | 128/700 |
| 4,922,909 | 5/1990 | Little et al. | 128/630 |
| 5,235,510 | 8/1993 | Yamada et al. | 364/413.02 |
| 5,331,552 | 7/1994 | Lloyd et al. | 364/413.15 |
| 5,365,428 | 11/1994 | dePinto et al. | 128/700 |

*Primary Examiner*—Marvin M. Lateef
*Assistant Examiner*—Brian L. Casler
*Attorney, Agent, or Firm*—Lyon & Lyon

[57] ABSTRACT

A motion video system and method for use with diagnostic imaging systems for combining the acquisition, display, and processing of digital video in real-time with physiological data indexing through the use of a mass storage device and digital motion video data compression/decompression, and for delivering video sequences of anatomy or graphical representations of physiological processes. The system comprises components or subsystems that operate to reduce the data content of the diagnostic video data using compression methods, assign physiological timing events, or physiological indexes, to pictures in sequence, create physiologically meaningful digital video loops, enhance visualization of the video data through spatial and temporal domain processing, as well as side-by-side real-time video displays, and archive compressed diagnostic video on a mass storage device.

18 Claims, 9 Drawing Sheets

MOTION VIDEO TRANSFORMATION SYSTEM AND METHOD

This application is a continuation in part of Ser. No. 08/158,157, filed Nov. 24, 1993, now abandoned which is a continuation of application Ser. No. 07/791,962 filed Nov. 12, 1991 now abandoned.

(C) 1994 S. M. Lobodzinski Ph.D. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright whatsoever.

FIELD OF THE INVENTION

This invention relates to a Motion Video Transformation System (MVTS) and methods used in medical fields such as cardiology, radiology, dentistry, neurophysiology, etc., and more specifically, to a transformation system and method for combining the acquisition, display, processing and storage of digital motion image sequences in real-time with physiological data indexing through the use of a mass storage device and real time digital video data compression and decompression

BACKGROUND OF THE INVENTION

Diagnostic advances in the field of medical imaging coupled with technological progress in digital storage media, digital processing of video, as well as audio data and Very Large Scale Integration (VLSI) device manufacturing, are converging to make the display, archiving, and transmission of digital video economical in a wide variety of medical applications.

Buffering, storage, and transmission of digitized video is a desired and critical feature for most medical applications. Because uncompressed digital video requires large amounts of bandwidth, memory, and storage space, video image compression is vital in the design of economically feasible display and archiving systems.

Recent studies of compressed cardiac ultrasonic and X-ray still images suggest that compression techniques have the potential to offer a compromise between traditional image recording techniques and economics of real-time diagnostic video compression. The advances in lossless and lossy video compression algorithms will further improve the quality of compressed video in the future.

Unlike in ordinary video signals, medical applications require a precise correlation of every video frame in a video sequence to physiological events occurring in the imaged anatomies or processes, and further require an adaptive adjustment of the frame rate to suit these display requirements. It is therefore diagnostically advantageous to think of a diagnostic video as a sequence of digital video events, each corresponding to a physiological phenomenon such as a heart contraction or relaxation.

For example, the practice of ultrasonography requires video recording of patient data for diagnostic and record keeping purposes. A typical ultrasonographic study comprise a small number of still images and few minutes of full motion video recording. Also, in special applications, the simultaneous display of multiple cardiac cycles, such that side-by-side comparisons of previously recorded video sequences can be made with live video sequences, is required during an examination for diagnostic purposes.

Often times, access to patient records in the form of digital motion video is required so that physicians of various specialties located in different areas can participate in the diagnostic or review process concurrently.

Although most diagnostic imaging systems provide some sort of cine' loop review, they typically do not provide digital motion video recording, serial comparison, and display functions. Typically, the video recording is accomplished by professional grade video tape recorders using Super-VHS (S-VHS) format tapes attached to the diagnostic imaging system (DIS).

Diagnostic video is recorded at a constant frame rate (FR) (typically 30 frames per second or fps) onto the video tape, and bears no relevance to the physiological function of the imaged anatomy or process, such as cardiac cycles. A tedious manual process is required to search through the video tape to identify the appropriate video frames corresponding to the systole or diastole. The video taped echocardiographic examination data, such as patient name, identification number, machine settings, etc., are available only in a visual format. In other words, this information cannot be used for databasing applications.

On the whole, the diagnostic video review process is very time consuming and difficult due to the operational limitations of the video cassette recorder. Copies of originally recorded diagnostic video result in image resolution degradation which renders them more difficult to interpret accurately. Also, video tapes require a lot of storage space, and degrade further with time. Thus, video tapes are not an ideal media for medical record keeping.

In another example, angiographic coronary arteriography and ventriculography studies are performed either to diagnose the presence of heart disease or to aid in a procedure called Percutaneous Transluminal Coronary Angioplasty (PTCA).

Although digital motion video capture and visualization systems for X-ray angiography do exist, they are significantly different from the system to be described herein. The present day digital angiography systems do not utilize real-time video data compression, nor do they store routinely data from the completed studies to a removable mass storage media. Rather, the images are stored to a large random access memory (RAM) based image buffer for instant replay and visualization. Only selected still images of arteriograms and venriculograms are archived to an optical disk. The size of the buffer varies, but rarely exceeds 120 seconds worth of full motion video. The images are also simultaneously recorded on 35 mm cine' film for archiving. The digital angiography motion image review systems usually allow for repetitive visualization of single contrast injections, but do not allow for visual serial comparisons of selected cardiac cycles from different contrast injections.

More recent X-ray imaging equipment currently utilizes charge coupled devices (CCD) in place of traditional fluoroscopy, with full digital image archiving of uncompressed digital motion video to a high bandwidth video tape recorder. However, the high cost of such recorders limit their application to playback on dedicated workstations only, and does not allow for digital video image transmission, serial comparisons, and display in a multiple window fashion. The availability of multiple cardiac cycle display would be particularly useful during a PTCA procedure so that the progress of plaque removal from the arteries (called revascularization) can be monitored.

Furthermore, in the standard practice of coronary angiography, a 35 mm cine' film recording is always made, regardless of any digital image storage capability, due to the need for inexpensive means of image review and overreading by a referring physician. Thus, since the patient examination data is typically available only in the cine' film and the digital media format, it is impossible or very difficult to integrate all of the pertinent data into digital transmission networks.

Real-Time Video Compression

Motion video compression techniques are based on one of two basic compression methods. The first method is the intra-frame compression method, and the second method is the inter-frame compression method.

In the intra-frame method, all of the compression is accomplished within a single video frame, whereas in the inter-frame process, all of the compression is accomplished between successive video frames since many areas in video frames often do not change from one frame to the next.

Several international standards for the compression of digital video signals have emerged over the past decade, with more currently under development. Several of these standards involve algorithms based on a common core of compression techniques, such as the Consultative Committee on International Telegraphy and Telephony (CCITT) Recommendation H.120, the CCITT Recommendation H.261, the ISO/IEC Joint Picture Expert Group (JPEG) standard, and the Moving Picture Experts Group (MPEG) standard. The MPEG algorithm was developed as part of a joint technical committee of the International Standards Organization (ISO) and the International Electrotechnical Commission (IEC).

Need For Compression

A typical color video frame (640×480×24 resolution) produced by a DIS consists of 307,200 pixels, wherein each pixel is defined by 24 bits (one of 16.7 million colors), thereby requiring 921,600 bytes of memory. To archive one minute of National Television Standards Committee (NTSC) motion video, for example, one needs 27,648,000 bytes of memory. Clearly, these requirements are outside the realm of realistic storage capabilities in diagnostic medicine.

Furthermore, the rate at which the data needs to be stored and retrieved in order to display motion vastly exceeds the effective transfer rate of existing storage devices. Retrieving full motion color video at a rate described above (30 megabytes/sec) from present day hard disk drives, assuming an effective hard disk transfer rate of about 1 megabyte per second, is 30 times too slow.

From a CD-ROM, assuming an effective transfer rate of 150 kilobytes per second, the rate is about 200 times too slow. Technological progress in the area of image compression techniques resulted in methods of video compression aimed at reducing the size of the data sets while retaining high levels of image quality.

From the point of view of video bandwidth considerations, video compression methods can be grouped into two categories. The first category results in data loss and is called the lossy method. The second category does not lose data and is called the lossless compression method. The lossy compression method does not preserve all of the information in the original data, but it can reduce the amount of data by a significant factor without affecting the image quality in a manner detectable by the human eye. The lossless image compression method allows for the mathematically exact restoration of the image data. However, in order to achieve high compression ratios and still maintain a high image quality, computationally intensive algorithms must be relied upon. A real time (compression of each frame performed in less than xmilliseconds) video compression may be implemented using a number of techniques known in the art. Due to the attractiveness of standardized compression methods, several implementation solutions are currently available.

Balkanski, et. al., U.S. Pat. No. 5,253,078, discloses the implementation of a data compression/decompression system using a discrete cosine transform (DCT) and its inverse transform (IDCT), which are provided to generate a frequency domain representation of the spatial domain waveforms representing the video image. This technique is known as a motion JPEG compression.

Gonzales, et. al, U.S. Pat. No. 5,231,484, discloses another implementation method for MPEG standard which relies on predictive/interpolative motion-compensated hybrid DCT/DPCM coding and quantization of the digital cosine transform (DCT)coefficients.

Another efficient motion image compression technique is disclosed by Israelsen, U.S Pat. No. 5,247,357, wherein vector quantization allows for compression ratios ranging anywhere from 20:1 to 100:1. Vector quantification efficiency stems from its role as a pattern-matching algorithm, in which an image is decomposed into two or more vectors, each representing particular features of the image that are matched to a code book of vectors and coded to indicate the best fit.

As the technology develops, other image compression techniques will emerge in the future which may find application in the methods and system described herein, and such use is contemplated.

Digital archiving of uncompressed digital video data directly from a display buffer of diagnostic imaging systems (DIS) is also possible on certain models. An example of such system is an ultrasound imaging system such as the Hewlett-Packard Sonos 1500. The digital video data is available in a digital format at the output of the Sonos 1500 in an uncompressed format for external storage to a disk media. Digital video is written directly to a magneto-optical disk drive for storage.

The image acquisition is gated by the R wave of ECG and recorded at 30 frames per second to the disk. A typical cine' loop of 30 frames requires 40 megabytes of disk space. The system of the present invention differs significantly from the Sonos 1500 since the functions of system of the present invention relate to video processing and visualization through the use of video transformation techniques. In particular the system of the present invention provides real-time video and audio compression/decompression, temporal domain processing, continuous video indexing with physiological signals, and synchronized real-time serial comparisons of previously recorded video with archived studies, as well as live videos. Furthermore, as a benefit of real-time video compression, the system of the present invention can store significantly more studies to the storage media than Sonos 1500. For example, if MPEG-1 compression algorithm is used for video compression, the amount of storage required for a full frame one cardiac cycle consisting of 30 frames is approximately 200 kilobytes as compared to 40 megabytes required by Sonos 1500.

In another specific ultrasonography application called stress echocardiography known in the art, short digital video clips corresponding to single cardiac cycles are field-frame grabbed synchronously with ECG to the solid state memory of the computer. Due to the large amounts of solid state memory required for uncompressed digital video, only portions (areas of interest) of the displayed even or odd fields can be acquired, beginning with 50 millisecond delay after the detection of a gating signal (ECG pulse output). Manual "grab" initiates the acquisition process. If the operator misses the optimal acquisition time, the critical information may be lost resulting in a non-diagnostic test. The number of cine' loops in the solid state memory is usually less than 60 for a total number of frames of 480. The visualization or display of the digitized cine' loop is possible only after post processing and the number of loops displayed in a side-byside fashion is limited to four. The cine' loops cover approximately 450 milliseconds of the cardiac cycle, which for a slow beating heart, is usually limited to a systole. A typical protocol allows for 8 fields per cycle with an interframe delay of 50 ms. Selected systolic cycles comprising of 8 field each and corresponding to echocardiographic views acquired at different stages of the exercise protocol are then displayed in the form of a "quad screen", i.e., four cycles at a time.

Complete stress echocardiography studies consisting of 2 or more sets (e.g. pre-exercise and post-exercise) of data for areas of interest of four echocardiographic views comprising eight fields each could be fitted in a 1.44 megabytes floppy disk, or an optical disk drive after run length encoding. The "video" storage to disk and retrieval are not real-time.

An example of a stress echocardiography system described above is the Dextra DX, by Dextra Medical Inc.

The methods of the present inventions are distinctively different from the described methods of stress echocardiography. The system of the present invention utilizes real-time image compression to store digitized video to a disk media in a continuous real-time fashion thus making it possible to store the entire study with no possibility of losing data. The amount of to video stored on a disk media could be as much as 60 minutes, thus resulting in hundreds of thousands of frames. Also the system of the present invention acquires physiological signals, such as ECG or blood pressure, continuously and simultaneously with video, thus making it possible to perform real-time video temporal domain processing and display while preserving full information in recorded video. The side-by-side display of diagnostic video in scalable windows in the system of the present invention can accommodate more than four independent bit streams played back directly from the storage media, unlike the stress echo systems which can display only the content of the solid state memory. Thus, in discussing the background of the invention above, one can appreciate the need for a device which will address the problems with the current practice of medical digital motion video image recording and display. There is a need for providing an apparatus and method for combining the acquisition, display, and processing of diagnostic digital video in real-time with physiological data indexing through the use of a mass storage device and real-time digital motion video data compression and decompression.

SUMMARY OF THE INVENTION

The Motion Video Transformation System (MVTS) and method of the present invention attempts to provide a system and method for combining diagnostic digital motion video acquisition, display, and processing with physiological data indexing through utilization of techniques of digital motion video compression through domain transformation.

The MVTS and method of the present invention utilizes video compression/decompression (video transformation) as an algorithm implemented on a video processor using one or more of the various compression methods known and available in the art.

Without limiting the scope of the present invention and its numerous applications in the field of medicine, an example of the present invention is described wherein the diagnostic imaging system is an Ultrasound System (US), otherwise known as an ultrasonograph, and is used in the context of cardiac imaging.

The MVTS and method of the present invention can be viewed as a medical video processing, visualization, archiving, and telecommunication system suitable for use with medical imaging devices delivering motion video pictures of anatomy, or graphical representations of physiological processes. The MVTS comprises components or subsystems that operate to: (1) reduce the data content of motion video sequences using digital motion video compression methods known in the art; (2) assign physiological timing events to the video frames in a sequence; (3) create physiologically meaningful digital motion image loops based upon these physiological timing event indexes; (4) enhance the display of video data through spatial and temporal domain processing; (5) store compressed diagnostic video to a commonly available mass storage device in real-time; (6) retrieve the compressed diagnostic video from the common mass storage device in real-time; (7) provide means for incorporation of compressed digital motion video into a computerized patient record; and (8) provide means for tele-consultations, diagnosis, and video data interchange with Digital Image Communications in Medicine (DIACOM)-compatible devices, or other similar means, over common data links.

More specifically, one component implements real-time video frame indexing with one or more physiological timing event markers or physiological signals. The video indexing operations are applied independently of digital motion video compression which reduces the image data bandwidth while retaining optimal visual quality of the image.

Another component comprises a subsystem for performing digital motion video compression necessary to meet the target bit-rate for a particular application. Examples of such algorithms include, but are not limited to, motion JPEG, Wavelet, Vector Quantization, MPEG or other video compression standard.

Yet another component comprises the circuits necessary to input physiological signals and event markers, or timing indexes, to the processing system. Examples of such signals may include, but are not limited to, ECG, blood pressure, EEG, etc.

Yet another component comprises a computer with software implementing algorithms for temporal and spatial domain image processing, image attribute extraction from the video signal, optical character recognition from video signal, image formatting, video sequence and loop calculations, video archiving and video transmission.

Another component comprises a subsystem for implementing bi-directional signals for control and status sensing of imaging devices. The control signals allow the imaging devices and the system described in this invention to function together to timely display either playback or on-line data as responses to control keyboard commands.

Another component comprises a video display processor which allows for display of multiple digital motion video streams in respective scalable windows. This method applies to serial comparisons of digital motion video sequences, stress echocardiography and other modalities, requiring more than one video stream to be displayed simultaneously on the screen.

Another component comprises a set of peripherals such as video monitor, mass storage devices, data import/export circuits and pointing or remote control device connected to the computer. These peripherals provide means for compressed video image storage and transmission.

All cooperating components or subsystems operate compatibly with each other and each may be individually modified to accomplish the same task, without necessarily requiring the modification of any of the other subsystems.

The image indexing subsystem may be used by itself and each of the subsystems may also be used with other digital motion video image implementations such as uncompressed digital video.

Another significant difference is the ability of the system of the present invention to provide frame accurate rapid random access to archived digital video streams and real-time playback.

Accordingly, it is an object of the present invention to provide a new and improved system and method for real-time high resolution digital recording of full motion compressed color diagnostic imaging motion video indexed with physiological markers, such as EGG or blood pressure, to a common mass storage device.

It is a further object of the present invention to provide a system and method for faster video review and diagnostic process through random access to specific frames, cardiac cycles or selected digital motion video sequences, as well as instant playback of previously compressed still and full motion digital video.

An additional object of the present invention is to provide automatic extraction of video attributes from on-screen data such as patient name, identification number, calibration information, display mode, etc., for automatic digital motion video sequence indexing and archiving into a database.

Another object of the present invention is to provide a system and method for creating a complete digital motion video history archived onto an inexpensive high capacity digital removable media as an alternative to video tape and cine' film.

Yet another object of the present invention is to provide improved visualization of angiographic digital motion video with synchronous display of cardiac cycles from different injections.

Still another object of the present invention is to provide for an integrated cardiac ultrasound and angiography digital motion video database for archival and retrieval.

Another object of the present invention is to provide medical digital motion video such as ultrasonic and angiographic data in physiologically determined sequences, displayed simultaneously in multiple scalable windows for improved display and serial comparisons.

A further object of the present invention is to provide for transmission of digital full motion medical studies through remote data links or Local Area Networks utilizing HL-7, DIACOM, or other similar standards.

Further objects and advantages of the present invention will become apparent from a consideration of the drawings and ensuing description.

DESCRIPTION OF THE PREFERRED EMBODIMENT

Figure 1:
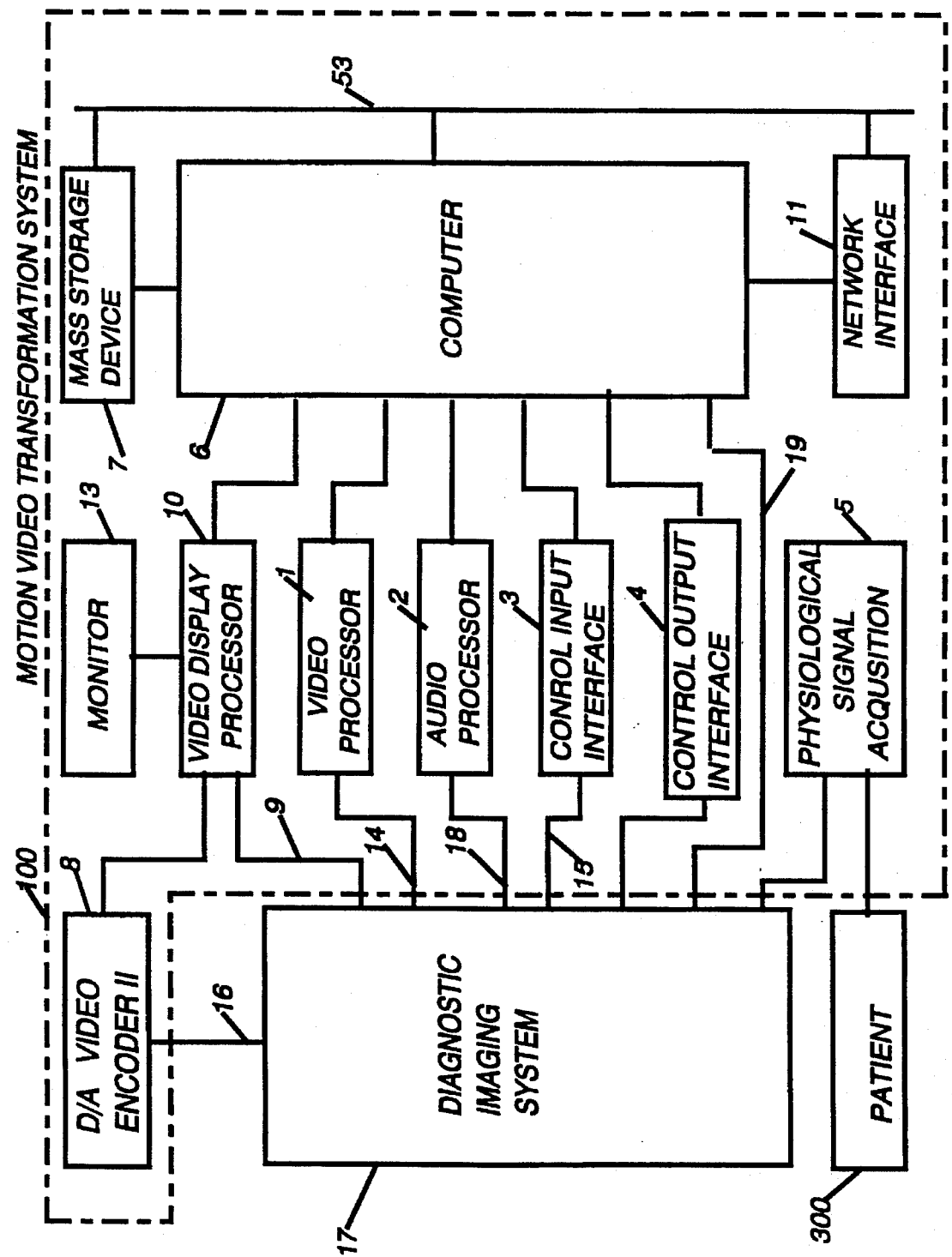
FIG. 1 is a block diagram of the MVTS of the present invention.

A preferred embodiment of a Motion Video Transformation System (MVTS) 100 of the present invention is shown in FIG. 1, and the operation of the MVTS 100 is as follows. A Diagnostic Imaging System (DIS) 17 generates a video signal 14. The DIS 17 can be a standard original equipment manufacturer's apparatus such as an Ultrasound System (US) 200, otherwise known as an ultrasonograph. Other DIS 17 may be an X-ray angiography system, a cardiac Magnetic Resonance Imaging (MRI) apparatus, or other medical or non-medical diagnostic imaging apparatus. The video signal 14 can be generated in either analog or digital format.

A Video Processor (VP) 1 is in communication with the DIS 17 for receiving the video signal 14 from the DIS 17. The main function of the VP 1 is to reduce the bandwidth of the video signal 14 being generated by the DIS 17. Other functions which may be performed by the VP 1 include conversion and encoding of the video signal 14 from the DIS 17 to a format readable by a computer 6, as well as data formatting, scan conversion, and optical character recognition.

If Doppler flow imaging is used, an audio Doppler signal 18 becomes an essential part of the diagnostic data. The Doppler sound complements the diagnostic information in the video signal 14 of the DIS 17. An audio processor (AP) 2 is used to quantize and then compress the audio Doppler signal 18.

Audio compression/decompression can be carried out by a Digital Signal Processor (DSP) (not shown) such as the Motorola 5600, the Texas Instruments 3200 family, or an equivalent DSP. In a preferred embodiment of the MVTS 100, the ISO MPEG (2-11172) method with two channels and variable compression rates from 32 to 384 kilobytes per second, to achieve frame synchronized audio compression, is implemented in the DSP.

A control input interface 3 circuit senses control signals 15 which are generated by the DIS 17. These control signals 15 may include ON/OFF signals intended for an external Video Cassette Recorder (VCR) (not shown) such as record, pause, playback, rewind, fast forward, etc.

Figure 2:
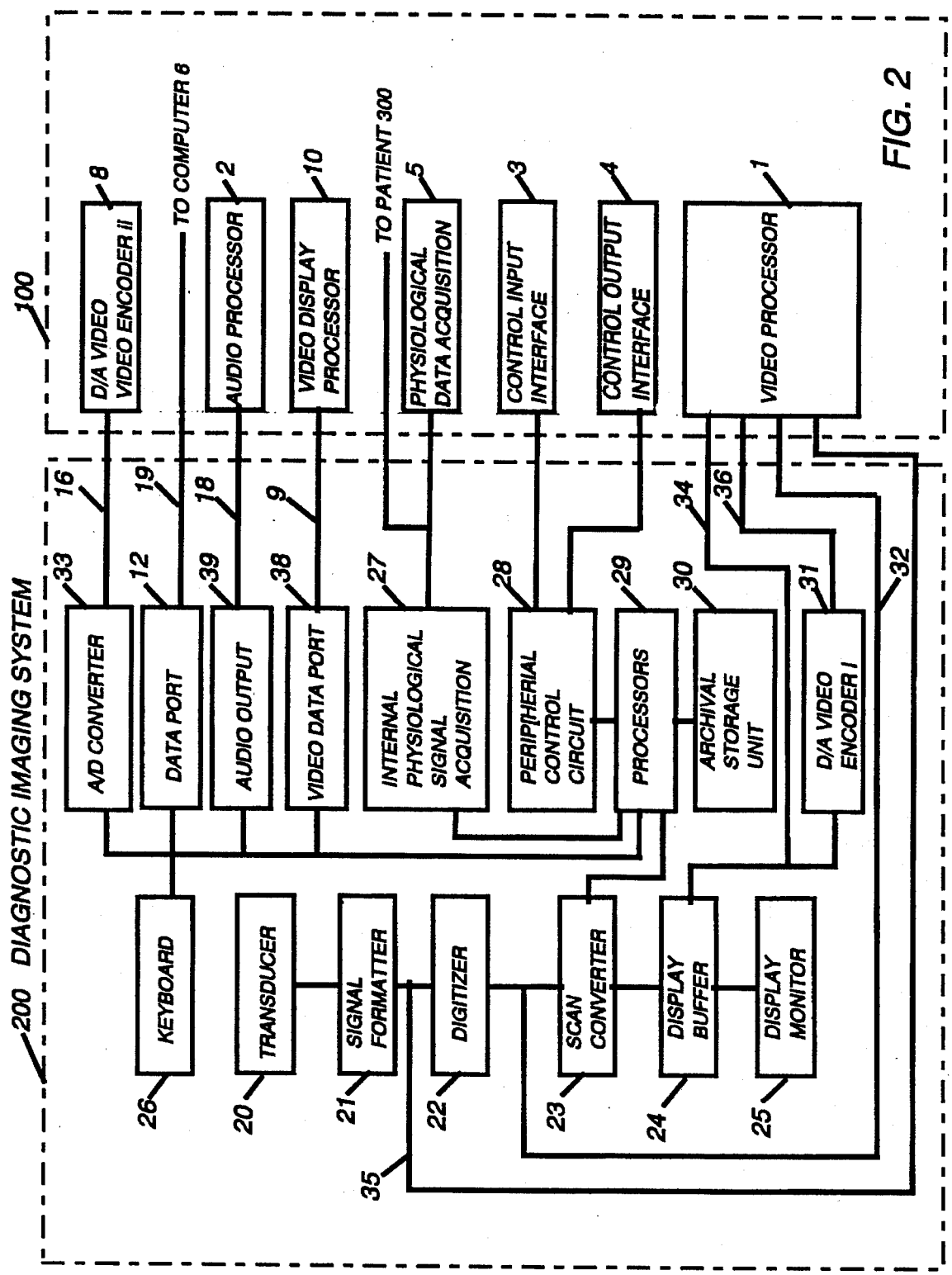
FIG. 2 is a block diagram of a portion of the MVTS of the present invention wherein the diagnostic imaging system is an Ultrasound System (US).
Figure 9:
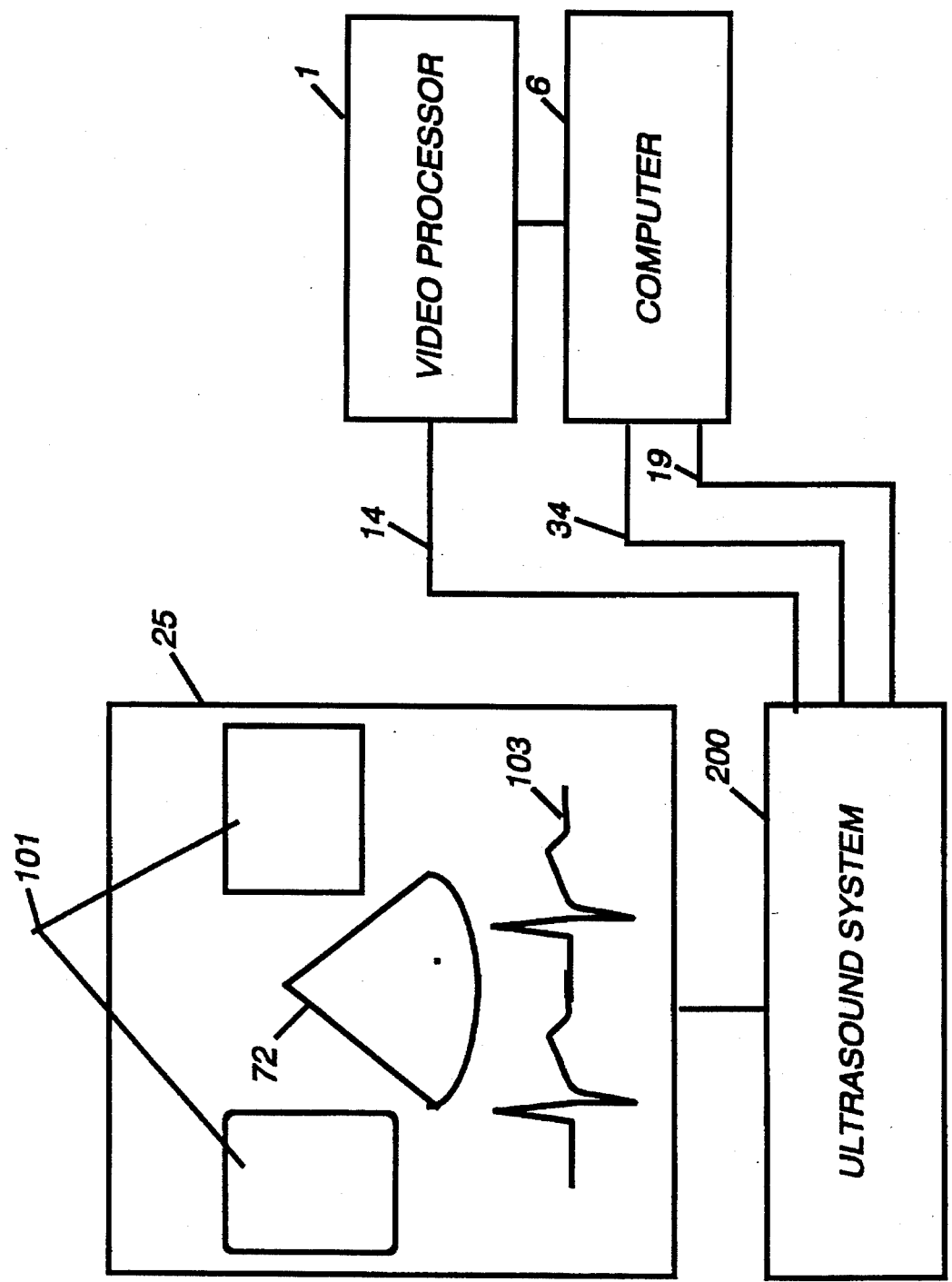
FIG. 9 is an illustration of a video display showing display attribute data which can be processed for databasing purposes.

Referring to FIG. 2, as well as FIG. 1, upon sensing these control signals 15, the MVTS 100 of the present invention is able to perform control functions such as playback, rewind, stop, pause, or record, which are already implemented in the control structure of the DIS 17 and are intended for the external VCR. By capturing these control signals 15, the MVTS 100 can respond to the commands requested by an operator of the DIS 17 from its keyboard 26. A data port 12 is intended for supplying display attribute data 101 (as shown in FIG. 9) over a data link 19.

A control output interface 4 circuit is provided for controlling certain functions of the DIS 17 from an external device such as MVTS 100 which can be attached to the DIS 17.

For example, DIS 17 will display an MVTS 100 analog video output signal 16 from a D/A video encoder II 8 on an internal display monitor 25 (FIG. 2) if the status of MVTS 100 as signaled by control output interface 4 is "playback". The MVTS analog video output signal 16 is used as an input to DIS 17, which in FIG. 2 is an Ultrasound System (US) 200. The D/A video encoder II 8 converts digital display video signals into an analog format, such as composite NTSC, S-Video or RGB.

A Physiological Signal Acquisition (PSA) 5 circuit amplifies and converts the patient's 300 physiological signals such as but not limited to ECG, blood pressure and blood flow to a form suitable for processing by the computer 6. These signals carry information such as timing, function and state of the processes and phenomena taking place in imaged anatomies.

An example of physiological signal utilization by the MVTS 100 is an electrocardiogram which accurately times the heart contraction (systole) through detection of the QRS complex in the ECG signal. In case of arrhythmias, a blood pressure signal may be used as a marker, or physiological index, of cardiac events.

Timing the correlation of a video frame rate (FR) with physiological signals used for indexing is critical in applications such as stress echocardiography, stress radionuclide angiography, or contrast echocardiography studies.

The computer 6, in a preferred embodiment, is a standard original equipment manufacturer's computer with the following: (1) at least 8 megabytes of random access memory (RAM); (2) the capability for handling data transfer rates on a video display bus of at least 33 megabytes per second; (3) a dedicated I/O port; and (4) a mass storage controller (hard disk, optical disk, video tape) capable of handling at least 10 megabits per second sustained transfer rate between the computer memory and the storage media.

Examples of such a computer include, but are not limited to, an IBM compatible x86 processor system, an Apple Quadra 620 or higher, an IBM Power PC, and a Sparcstation 10 from Sun Microsystems. The function of the computer 6 is to provide system control, communication, display, and video storage functions for the MVTS 100.

A mass storage device 7 may be one or more of the various standard original equipment manufacturer's disk storage devices, such as magneto-optical recordable optical disks, digital audio tape, and Winchester disk drives. The mass storage device 7 must be able to provide a minimum sustained data transfer rate of 150 kilobytes/sec.

As shown in FIG. 1, the output of the VP 1 is passed to a Video Display Processor (VDP) 10. The VDP 10 computes the correct timing for displaying a video at a desired resolution on an external display monitor 13.

A Network Interface (NI) 11 is provided for facilitating the exchange of compressed video and audio data over either Local or Wide Area Networks (LAN/WAN). In a preferred embodiment, various network protocols such as TCP/IP, NetWare, and other similar protocols are supported by the MVTS 100. A data bus 53 provides for the interconnection of the computer 6, the mass storage device 7 and the NI 11 components.

Turning back to FIG. 2, a portion of the MVTS 200 is shown wherein the DIS 17 of FIG. 1 is the Ultrasound System (US) 200, such as the Sonos 1500 sonograph manufactured by Hewlett Packard.

FIG. 2 illustrates the components of a typical ultrasonograph, as embodied by the US 200. The US 200 system comprises a transducer 20 which receives echoes reflected by the patient's 300 body organs. The echo signals are processed by a signal formatter 21 which converts them into an analog Radio Frequency (RF) signal 35. The analog RF signal 35, in an analog form, contains the information about imaged anatomical structures. The analog RF signal 35 is then digitized in a digitizer 22 which converts it into a form suitable by a scan converter 23. After additional processing and scan conversion in the scan converter 23, the resulting diagnostic video signal is passed to a display buffer 24 and can be displayed on the US 200 internal display monitor 25. An A/D converter 33 is used to convert the MVTS 100 analog video output signal 16 from an external device into a form suitable for display on the display internal monitor 25. The data port 12 is used to output the display attribute 101 data. A video data port 38 is intended for accepting an external video signal 9 in digital format for display on the internal display monitor 25.

Processors 29 of the US 200 control all operations of the US 200. An internal physiological signal acquisition 27 circuit is provided for displaying ECG and blood pressure data in graphical format together with diagnostic video information on the internal display monitor 25. The keyboard 26 is used for issuing control and operational commands to the US 200. A peripheral control circuit 28 is used for interfacing external devices (not shown) such as printers, and VCRs. The US 200 is also capable of archiving uncompressed digital video to an archival storage unit 30. An audio output 39 circuit provides Doppler sound audio and a "beep" which is an audio burst corresponding to the ECG R wave.

The MVTS 100 may acquire the analog RF signal 35 directly from the signal formatter 21 prior to the scan conversion which takes place in the scan converter 23. The VP 1 digitizes the analog RF signal 35, performs video compression, and then stores the data to the mass storage device 7, which can be of removable kind. A digitized RF signal 32 may also be used as an input to VP 1.

The ability to process the digitized RF signal 32, and the analog RF signal 35 is important in "contrast echocardiography studies" where raw echo signals are analyzed. Contrast imaging modality requires careful preservation of all RF signal components, and longer recording periods are needed.

Another application of the MVTS 100 to the field of ultrasonography can be achieved by utilizing an output digital video signal 34 from the US 200 display buffer 24. The scan-converted output digital video signal 34 may be available directly from the display buffer 24. The output digital video signal 34 is then supplied directly to the VP 1 for compression.

Yet another application is the usage of the MVTS 100 in lieu of an external VCR to US 200. In one application, the US 200 has the capability of digitizing the MVTS analog video output signal 16 in A/D converter 33 shown in FIG. 2 for subsequent display on the internal display monitor 25. In another application, the US 200 has the capability of accepting the external digital video signal 9 via the video data port 38 shown in FIG. 2 for a subsequent display on the internal display monitor 25.

The scan-converted output digital video signal 34 is converted into an analog video signal by a D/A video encoder I 31 and a resulting US 200 video output analog signal 36 may be used as an input to the MVTS 100. The video output analog signal 36 may be in the form of NTSC composite, S-Video (Y/C), or RGB video signal in the form of a 525 line raster.

The VP 1 can accommodate a plurality of inputs from US 200. The manner in which the VP 1 processes the inputs will be described more fully hereinafter with particular reference to FIG. 3.

Figure 3:
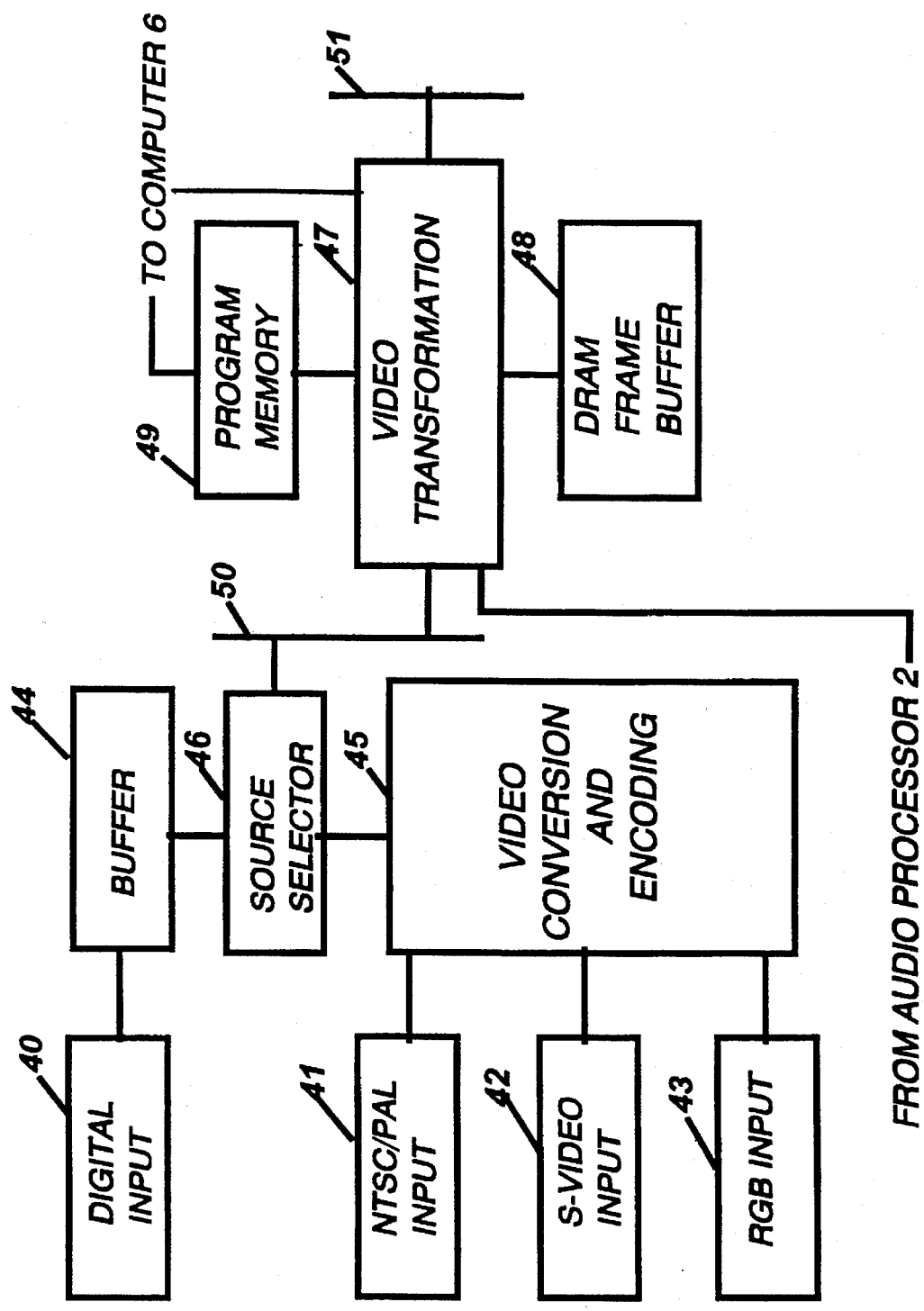
FIG. 3 is a block diagram illustrating the components of the Video Processor (VP) circuit of FIG. 1.

As shown in FIG. 3, which is a block diagram illustrating the components of the VP 1 circuit of FIG. 1, the VP 1 system may be functionally represented as comprising analog video buffers such as an analog video NTSC/PAL input 41, an S-Video input 42, and a RGB input 43. A video conversion and encoding circuit 45 performs the conversion and encoding of analog video signals to a form suitable for processing by a Video Transformation(VT) 47 processor. A digital input 40 which, in a preferred embodiment, may be a CCIR 601 serial component digital, a parallel interface such as SCSI-2, or other digital format is provided to supply digitized video data via a buffer 44 and a source selector 46 to the VT 47. The source selector 46 is used to switch between valid sources of video data.

The US 200 may encode additional information such as calibration and image format data into its video output analog signal 36 such as display format and image attributes.

The VP 1 is capable of extracting this information from the video output analog signal 36 (FIG. 2) after video conversion via the video conversion and encoding 45 circuit as shown in FIG. 3, and prior to video compression in the VT 47.

The VP 1 can be embodied in a Very Large Scale Integration (VLSI) circuit as a programmable single-chip device, or in discrete components such as but not limited to the IIT VCP (IIT Inc.) or CL-550 (C-Cube, Inc). The VT 47 processor has separate digital video buses, an input video bus 50 and an output video bus 51. The VT 47 processor uses a DRAM frame buffer 48 to store the uncompressed and reference images in the process of compression. The VT 47 uses a program memory 49 which provides code for video compression algorithms, post processing and control functions. The VT code is loaded by the computer 6 (FIG. 2) to suit a particular processing requirement.

In addition to video compression/decompression, a program residing in the program memory 49 supervises the VT 47 which also performs error correction on the compressed data, multiplexes the compressed audio and video data and parses the bit stream protocol. Depending upon the program, the VT 47 can act as a full H.261 codec, JPEG, MPEG 1, or MPEG 2 encoder/decoder. In addition to video compression/decompression functions, the VT 47 provides programmable video pre- and post-processing functions including video scaling, temporal filtering and processing, output interpolation, color conversion and multistream video display.

Due to the high computational power of the VP 1, a number of real-time image processing functions can also be implemented as needed. The examples of such functions may include colorization of selected frames, cycles or portions of thereof, as well as image filtering and image quantization.

According to the present invention, a video signal in any of the analog input formats 41, 42, or 43, or the digital input format 40, generated by the US 200 is passed via the buffer 44, the source selector 46, and the input video bus 50 to the VT 47 for compression. Additionally, the audio Doppler signal 18 produced by the US 200 and digitized by the AP 2 (FIG. 2) may be supplied to the VT 47 for multiplexing with compressed video. The video signal 14 and audio Doppler signal 18 compressed in VT 47 are outputted to the output video bus 51. In a playback video mode, the compressed video and audio from the mass storage device 7 (FIG. 1) is passed via the input video bus 50 to the VT 47 for decompression. Certain types of processors which may be utilized by the computer 6 may be capable of real time video and audio decompression if asymmetrical compression techniques such as MPEG have been used by the VT 47 to compress the audio Doppler signal 18 and video (41, 42, 43, 40) signals. The decompressed digital output is then forwarded to the VDP 10 (FIG. 1).

Figure 4:
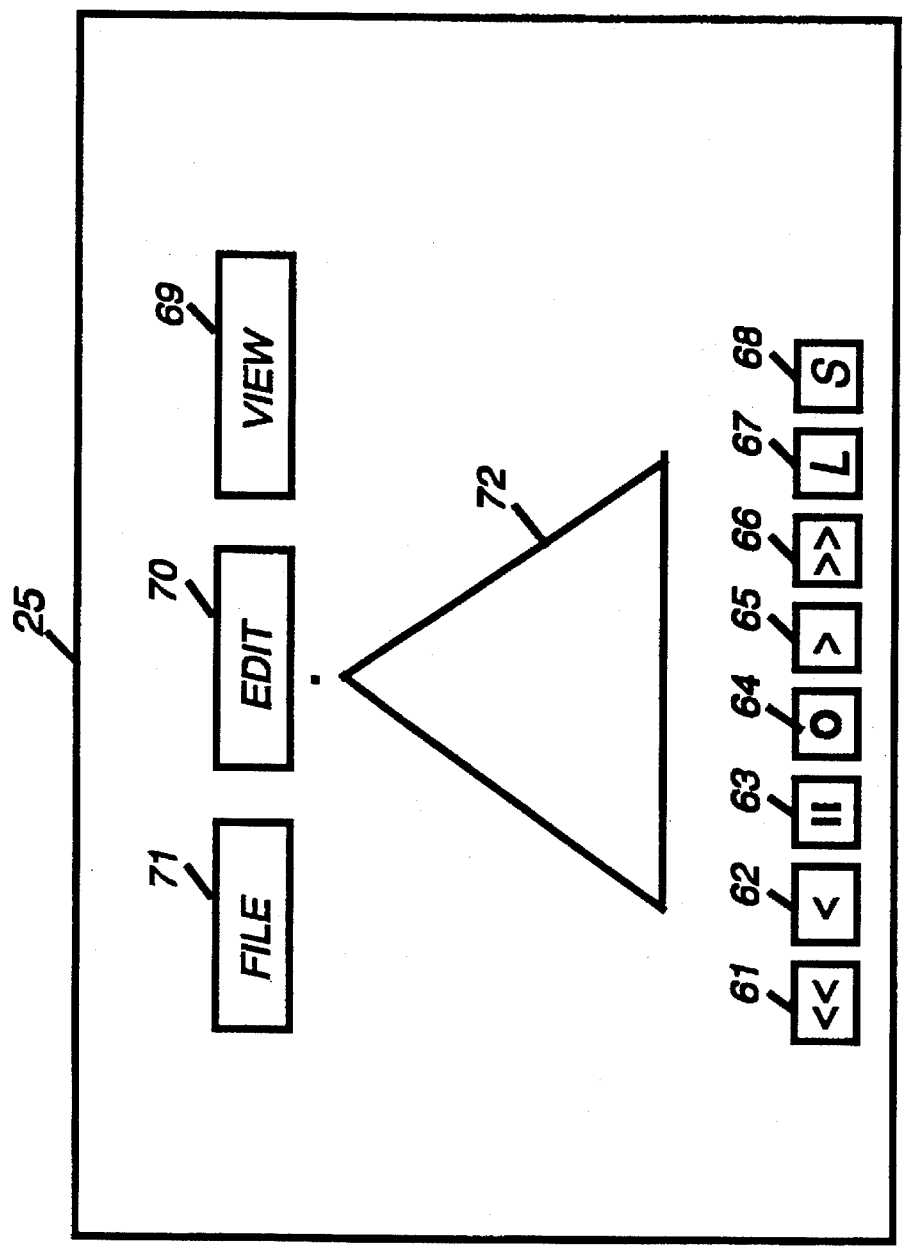
FIG. 4 is an illustration of a monitor display showing the software generated control buttons and their control functions.

Turning now to FIG. 4, software generated control buttons are displayed on either internal display monitor screen 25 or external display monitor 13. The display can be on the internal display monitor 25 of the US 200 if in an on-line mode, or on the external display monitor 13 of the MVTS 100 if in an off-line mode. A diagnostic video display 72 is shown as would be displayed on either the internal display monitor 25 (FIG. 2) or the external display monitor 13 (FIG. 1).

Referring to both FIG. 2 and FIG. 4, the selection of a record button 64 will begin the archiving of the digital video with underlying audio, physiological signals, and timing ECG marks to the mass storage device 7. The recording will continue until the selection of a stop button 68 or a stop issued by the control output interface 4 (FIG. 1). Fast rewind 61, single frame back 62, pause 63, fast forward 66, single frame forward 73 and loop 67 functions are also provided for video access and management in the customary manner.

Another function available in the MVTS of the present invention is the playback of recorded digital video and audio. The playback of compressed digital video and audio from the storage media 7 starts with the selection of a play button 65 and continues until the stop button 68 is selected or a stop control signal issued by control output interface 4 (FIG. 1).

As shown in FIG. 1, the computer 6 initiates playback process by retrieving compressed video data from the mass storage device 7 and passing it to the VP 1 for decompression. Decompressed video is then passed to the VDP 10. The playback modes include slow motion (inter frame interval longer than at the time of recording) and fast motion (inter frame interval shorter than at the time of recording). The access to playback functions which include a plurality of image display formats, such as slow motion, fast motion, display window size and frame rate is through a view button 69.

Video editing functions are activated after selecting an edit button 70, and include still frame selection, manual start and end of a video sequence. Manual editing functions are important in studies which have been collected from patients with cardiac rhythm disturbances.

Figure 5:
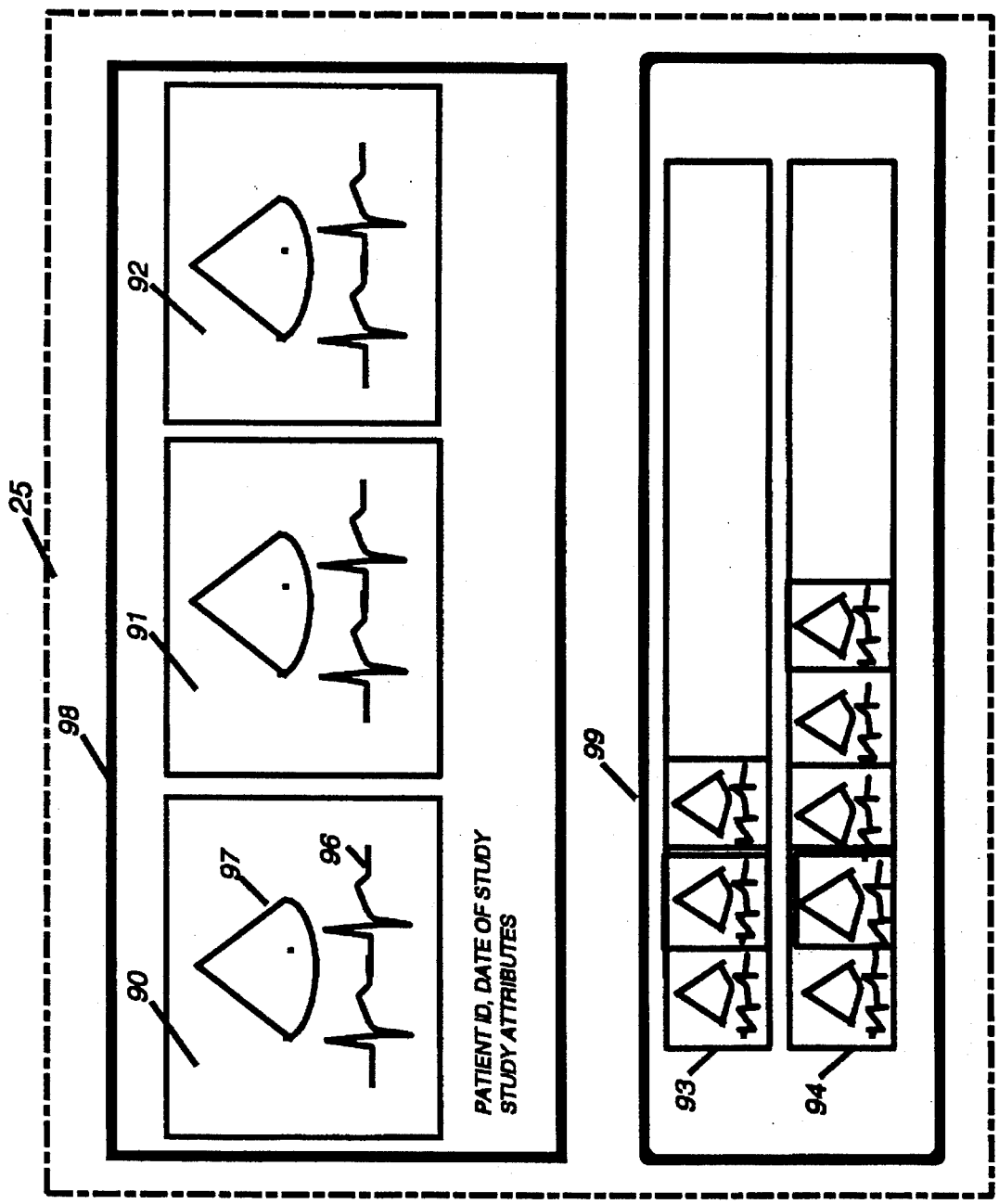
FIG. 5 is an illustration of a display screen format showing a visual catalog and a display area.

Access to archived studies is through a file button 71. The MVTS 100 may have a built-in database for archiving of compressed diagnostic video sequences 93 with embedded audio and physiological signals, single video frame images 94, display attribute data 101 and video attribute data 95 referenced in FIG. 5 and FIG. 9. Upon selection of this button, a visual representation of archived studies is displayed as shown in FIG. 5. A visual catalog 99 which can comprise a single video frame representation of an archived video sequence 93 and a single video frame image 94 is displayed in a "postage stamp" format shown in FIG. 5. The video sequences may represent different echocardiographic windows such as apical four chamber views, parasternal short axis views etc. A composition of a desired display format is accomplished by placing a selection from the visual catalog 99 in a display area 98. The process of selection is known as "drag and drop". If only one study has been placed in the display area 98, it will be displayed in a full screen format as shown in FIG. 4. If more than one selection has been made, the MVTS 100 will automatically adjust the display area to accommodate the selected video streams representing the diagnostic studies. A multiple video stream display is shown in FIG. 6.

For example, compressed diagnostic video sequences 90, 91 and 92 have been selected from the visual catalog 99 and placed in the display area 98. The compressed diagnostic video sequence 90 of FIG. 5 comprises a diagnostic video display 97, physiological signal display 96 and video attribute data 95. The MVTS 100 will dynamically assign the display space to these studies which will be displayed with the video attribute data 95. The video attribute data 95 includes patient demographics, image annotations and other data associated with the video sequence.

Figure 6:
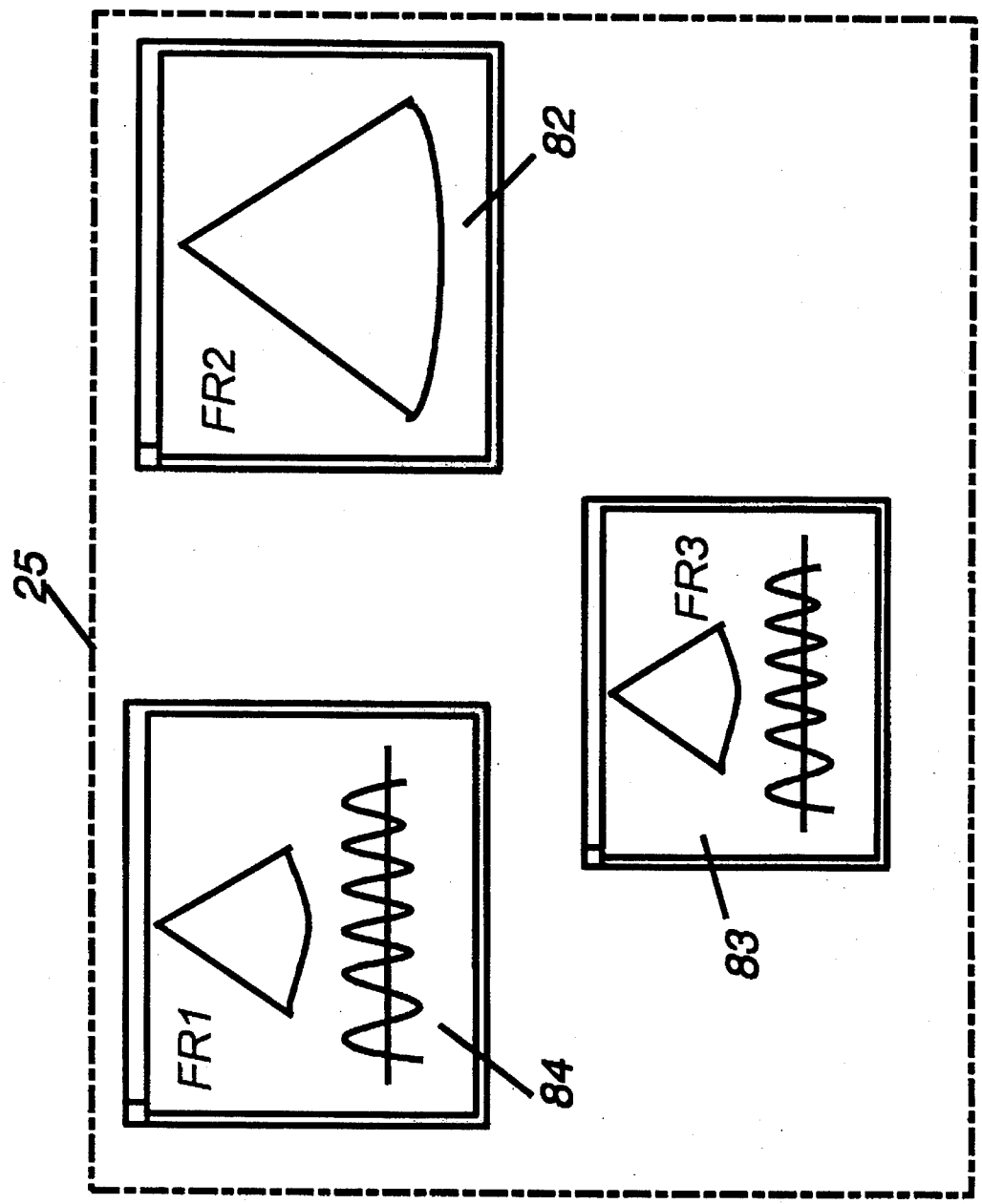
FIG. 6 is an illustration of multiple display window video streams scalable within the display area.

In applications where the display of a cardiac function is required, a plurality of digital video streams can be displayed simultaneously on the internal display monitor 25 (FIG. 2) or the external display monitor 13 (FIG. 1) as shown in FIG. 6. The display window of each video stream 82, 83, and 84 is fully scalable. The VDP 10 (FIG. 1) has the ability to change the size of the display window video stream within the display area of the monitor 25 and 13. The video stream display window 83 has a different size than the display windows of video streams 82 or 84. Each display window video stream may also be displayed at a different frame rate (FR). A frame rate FR1 for the display window video stream 84 may be different than a frame rate FR2 for the video stream 82 or a frame rate FR3 for the video stream 83.

Figure 7:
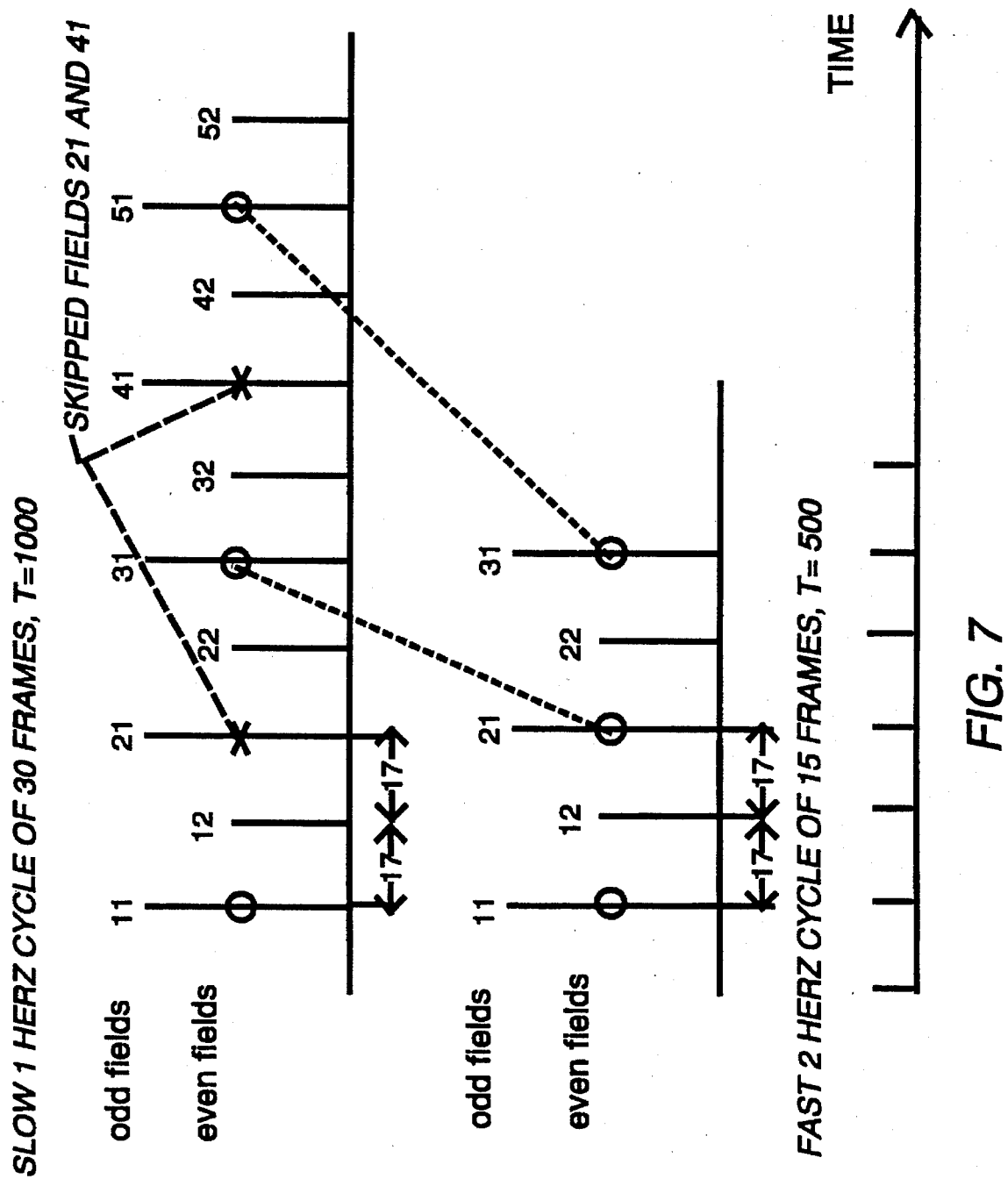
FIG. 7 is an illustration showing the synchronization of a slow and fast video cycle.

Referring now to FIG. 7, in order to visually synchronize periodic digital motion video segments such as cardiac cycles, they have to be displayed at the same speed, i.e., the temporal placement of the frames in the cycle must be the same and the inter-frame intervals must be preserved. Cycle synchronization is very important in stress echocardiography and X-ray angiography, where the patient management decisions are made from visual assessment of the cardiac wall motion and where the digital cycles of digital video sequences representing different projections are displayed simultaneously for comparison purposes.

The QRS timing from ECG or first derivative of the blood pressure may serve as a timing marker, or physiological index, in video signal annotation. The system first measures an average cardiac period for a given video sequence prior to data acquisition. A number of frames in each cycle will then be calculated as number of frames equals heart period divided by 33. Typically a sequence of video fields is grabbed from an interlaced video output analog signal 36 (as shown in FIG. 2). Each frame with its associated odd and even fields (11,12,21,22 etc.) will be numbered, starting with the first acquired frame, which is the end-diastolic for stress echocardiography applications, and its temporal position within a cardiac cycle will be stored together with compressed video data to the mass storage device 7 (FIG. 1).

The synchronization process of more than two video streams utilizes the same method as described by FIG. 7. The video streams comprise fields 11, 12, 21, 22, 31, 32, 41, 42, . . . 51, and are spaced evenly by 17 millisecond (ms) intervals in a slow cycle with a period of T=1000 ms. The odd fields are s11, s21, s31 and even fields are s12, s22, s32. In order to synchronize a faster cycle video stream with a period of T=500 ms with the slow cycle, only every other field of the slow cycle will be displayed simultaneously with the fast cycle in the following manner: s11 and f11; s31 and f21; s51 and f31 (wherein "s" designates the slow cycle and "f" designates the faster cycle), due to the smaller number of frames in the faster cycle.

Figure 8:
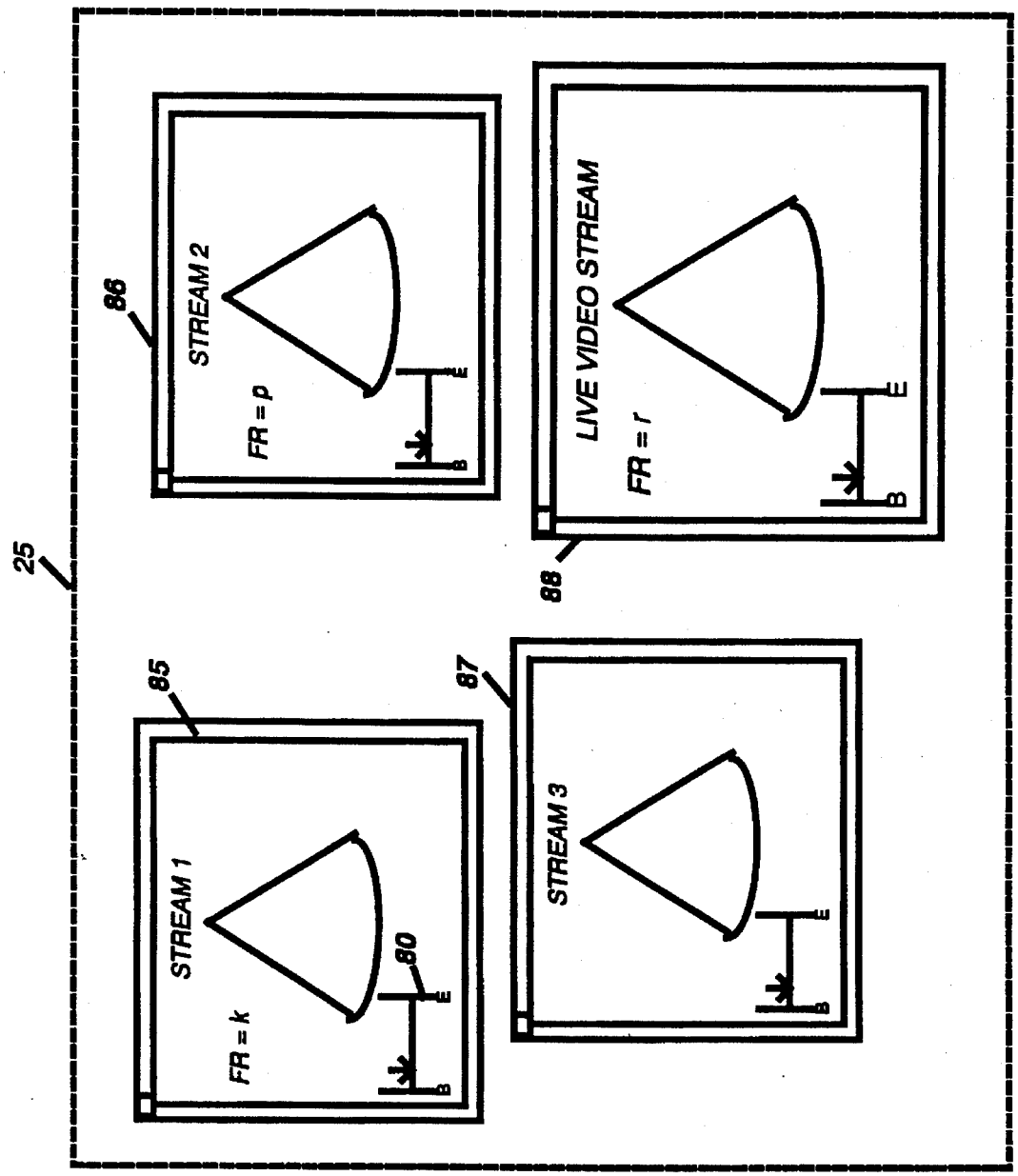
FIG. 8 is an illustration of a simultaneous multi-stream video display, including a live real-time video stream for comparison purposes.

The exact temporal locations of displayed frames in a slower cycle will be determined by the number of frames per cycle in the faster cycle. Since the display synchronization is a dynamic process, different frame configurations will be displayed differently depending upon the speed of the fastest cycle. It should be noted, that diagnostic video may be slower than 30 frames per second as exemplified by wide angle color Doppler displays. This method may be used for on-line serial comparisons of diagnostic video studies of archived (compressed) and live video. A method for display of full motion digital video data in a multiple window display format in a synchronized fashion is shown in FIG. 8.

Three digital video streams 85, 86 and 87, which have been previously selected from the visual catalog 99 as shown in FIG. 5, and a live video stream 88, are shown as displayed simultaneously on either the internal display monitor 25 or the external display monitor 13 in a synchronized fashion. An indexing arrow 80 shows the temporal location of the currently displayed video frame within the cardiac cycle, wherein B designates the begin of a cardiac cycle, and E designates the end of a cardiac cycle, corresponding to timing of the cardiac contraction.

Video streams may be recorded at different frame rates depending upon the DIS 17, wherein FR=k, p, q, and r. The number of frames in each cycle of the video stream is adjusted to fit the fastest rate within the multiple window display in a manner as explained with reference to FIG. 7.

Often times, a need arises to compare previously recorded video data with live video in a serial comparison. This is particularly important during a PTCA process or serial echocardiography studies. The synchronization of the video cycles from the storage with live video is accomplished by selecting a live video display format from view button 69 shown in FIG. 4. The selected display format as illustrated in FIG. 5 is complemented by a live video which is forwarded from DIS 17, via VP 1 to VDP 10 for display on an external monitor 13 as illustrated in FIG. 1. The methods of cycle synchronization, as explained in conjunction with FIG. 7, are applicable to live video synchronization in a serial comparison mode.

Tele-consultations and remote diagnosis are also important in practice of cardiac imaging, since the diagnostician may not be present at the imaging site. Examples of such applications include operating room imaging and mobile echocardiography. Because the bandwidth of diagnostic video after compression is significantly reduced (1.5 to 10 megabits per second (Mbps) depending on the compression method used by the VP 1), a network transmission of digital diagnostic video is possible over either local or wide area networks. The performance of digital video transmission over the network depends on the network operating system and the bandwidth of the link. A bandwidth of 15 Mbps (e.g. Ethernet protocol) is sufficient for real-time compressed video transmission. All functions of the disclosed MVTS 100 are available either in a multicast or point-to-point configurations over the described data links above.

Turning now to FIG. 9, to facilitate the transfer of pertinent information from the video recordings to a database, a video annotation method is used. A layout of a typical display contains display attribute data 101, diagnostic video display 72, and an ECG signal 103. In the US 200 system equipped with the data port 12, such as an RS-232 data port, the display attribute data 101 comprises the patient 300 data, along with the US 200 display parameter data, calibration settings and measurement data. This display attribute 101 is outputted via the data link 19 simultaneously with the diagnostic video. The computer 6 combines this information with compressed video data prior to storage to the mass storage device 7 (FIG. 1).

In US 200 systems which do not provide the data port 12, an Optical Character Recognition (OCR) algorithm is used to extract display attribute data 101 from the video display of the internal display monitor 25. The video signal 14 from the DIS 17 is forwarded to the VP 1 for processing and then to the computer 6. The display attribute data 101 is extracted from the video using OCR techniques and then combined in real-time with the digital video by the computer 6 prior to storage to the mass storage device 7 (FIG. 1).

The diagnostic video display 72, together with other patient 300 diagnostic information generated by MVTS 100 can be converted to a standard format such as American College of Radiology (ACR) and National Electrical Manufacturers Association (NEMA) (ACR-NEMA) Digital Imaging and Communications in Medicine (DIACOM) suitable for display on other DIACOM compliant medical diagnostic imaging devices.

While the above description contains many specificities, these should not be construed as limitations on the scope of the invention, but rather as an exemplification of preferred embodiments thereof. Many other variations are possible.

What is claimed is:

1. A motion video transformation system for communication with a diagnostic imaging system, said motion video transformation system comprising:

a computer;

a video processor in communication with said computer, said video processor for receiving and compressing a video signal generated by the diagnostic imaging system, thereby producing a compressed video signal;

a physiological signal acquisition circuit in communication with said computer, said physiological signal acquisition circuit for receiving physiological signals from a patient, said computer being programmed for combining and synchronizing in real-time said compressed video signal with said physiological signals to create a compressed indexed video signal, said physiological signals for providing a reference index in said compressed video signal via computer synchronization by correlating an event in said compressed video signal to a corresponding event in said physiological signals; and a mass storage device in communication with said computer, said computer being programmed for storing said compressed indexed video signal to said mass storage device.

2. A motion video transformation system for communication with a diagnostic imaging system, said motion video transformation system comprising:

a computer;

a mass storage device in communication with said computer;

a video processor in communication with said computer;

said video processor comprising a video processor input;

a video transformation processor in communication with said computer, said video processor input for receiving a video signal input from the diagnostic imaging system;

said video processor for converting said video signal input into video data for processing by said computer;

said video transformation processor for compressing said video data and providing a compressed video data to said computer;

a physiological signal acquisition circuit in communication with said computer for receiving physiological signals from a patient and converting said physiological data for processing by said computer;

said computer being programmed for combining and synchronizing in real-time said compressed video data with said physiological data into compressed indexed video data, said physiological data for providing a reference index in said compressed video data via computer synchronization by correlating an event in said compressed video data to a corresponding event in said physiological signals; and said computer being programmed for storing said compressed indexed video data to said mass storage device.

3. The motion video transformation system of claim 2, further comprising:

a display monitor in communication with said computer;

said computer being programmed for displaying a visual catalog on said display monitor and having means for displaying a plurality of video sequences in a display area of said display monitor;

said visual catalog comprising at least one video frame representation of video sequences previously stored on said mass storage device, wherein a selection of a specific video frame representation from said visual catalog will display a corresponding video sequence in said display area of said display monitor; and said video sequences being retrieved from corresponding compressed indexed video data stored in said mass storage device.

4. The motion video transformation system of claim 3, further comprising:

means for individually scaling in dimension within said display area at least one of said plurality of video sequences displayed in said display area of said display monitor.

5. The motion video transformation system of claim 3, further comprising a computer generated display comprising a plurality of control buttons on said display monitor for selecting a predetermined function to be performed upon at least one of said plurality of video sequences in said display are of said display monitor; and said computer being programmed for processing at least one of said plurality of video sequences according to said predetermined function upon selection of a corresponding control button.

6. The motion video transformation system of claim 5, further comprising:

a computer generated real-time control button on said computer generated display, wherein selection of said real-time control button provides a real-time video sequence display in real-time during acquisition of said video input from the diagnostic imaging system.

7. The motion video transformation system of claim 6, further comprising:

a network interface in communication with said computer, said network interface for providing a communications link with a remote computer wherein said remote computer has access to all functions available on said computer.

8. The motion video transformation system of claim 5, further comprising;

a video display processor;

said video display processor in communication with said video processor;

said display monitor in communication with said video display processor;

said computer being programmed for responding to the selection of a real-time control button from said plurality of control buttons on said display monitor by sending a real-time compressed indexed video data from said computer to said video transformation processor;

said video transformation processor for decompressing said compressed indexed video data, and providing uncompressed indexed video data to said video display processor; and said video display processor for computing an appropriate display format for displaying said uncompressed indexed video data at a predetermined resolution on said display monitor, said video display processor for displaying a video sequence in real-time during acquisition of said video input from the diagnostic imaging system.

9. The motion video transformation system of claim 5, further comprising:

a video display processor;

said video display processor in communication with said video processor;

said display monitor in communication with said video display processor;

said computer being programmed for responding to selection of a playback command by retrieving corresponding pre-recorded compressed indexed video data from said mass storage device corresponding to said video sequences which have been selected and providing said compressed indexed video data which corresponds to said video sequences to said video transformation processor;

said video transformation processor for decompressing said compressed indexed video data, and providing uncompressed indexed video data to said video display processor; and said video display processor for computing an appropriate display format for displaying said uncompressed indexed video at a predetermined resolution in said display area of said display monitor.

10. The motion video transformation system of claim 3, wherein said computer has means for receiving attribute data embedded into said video data; and said computer being programmed for processing said attribute data and for databasing and indexing said compressed indexed video data stored on said mass storage device.

11. The motion video transformation system of claim 2, further comprising:

a control input interface for providing the diagnostic imaging system with a means for controlling predetermined functions of said computer; and a control output interface for providing said computer with a means for controlling predetermined functions of the diagnostic imaging system.

12. A method of motion video transformation comprising the following steps:

generating a video signal from a diagnostic imaging system;

receiving a video signal input from the diagnostic imaging system;

converting said video signal input into video data for processing by a computer;

compressing said video data and providing compressed video data to said computer;

receiving physiological signals from a patient and converting said physiological signals into physiological data for processing by said computer;

combining and synchronizing in real-time said compressed video data with said physiological data into a compressed indexed video data by correlating events in said compressed video data with corresponding events in said physiological data; and storing said compressed indexed video data to a mass storage device.

13. The method of motion video transformation of claim 12, further comprising the following steps:

retrieving said compressed indexed video data from said mass storage device via said computer;

displaying a plurality of video sequences on a display area of a display monitor; and synchronizing said plurality of video sequences such that a predefined physiological cycle with a multitude of phases can be displayed for each individual video sequence wherein an exact temporal match of frames corresponds to the phases of said physiological cycle in said video sequences.

14. A motion video transformation system for communication with a diagnostic imaging system, said motion video transformation system comprising:

a computer;

a mass storage device in communication with said computer;

a video processor in communication with said computer;

said video processor comprising;

a video processor input;

a video transformation processor in communication with said computer;

said video processor input for receiving a video signal input from the diagnostic imaging system;

said video processor for converting said video signal input into video data for processing by said computer;

said video transformation processor for compressing said video data and providing a compressed video data to said computer;

a physiological signal acquisition circuit in communication with said computer for receiving physiological signals from a patient and converting said physiological signals into physiological data for processing by said computer;

said computer being programmed for combining and synchronizing in real-time said compressed video data with said physiological data into compressed indexed video data, said physiological data for providing a reference index in said compressed video data via computer synchronization by correlating an event in said compressed video data to a corresponding event in said physiological signals;

said computer being programmed for storing said compressed indexed video data to said mass storage device;

a display monitor in communication with said computer;

said computer being programmed for displaying a visual catalog on said display monitor and having means for displaying a plurality of video sequences in a display area of said display monitor;

said visual catalog comprising at least one video frame representation of video sequences previously stored on said mass storage device, wherein a selection of a specific video frame representation from said visual catalog will display a corresponding video sequence in said display area of said display monitor, said video sequences being retrieved from corresponding compressed indexed video data stored in said mass storage device;

a computer generated display comprising a plurality of control buttons on said display monitor for selecting a predetermined function to be performed upon at least one of said plurality of video sequences in said display area of said display monitor;

said computer being programmed for processing at least one of said plurality of video sequences according to said predetermined function upon selection of a corresponding control button; and a computer generated real-time control button on said computer generated display, wherein selection of said real-time control button provides a real-time video sequences display in real-time during acquisition of said video input from the diagnostic imaging system.

15. The motion video transformation system of claim 14, further comprising a network interface for providing a communications link wherein a remote computer has access to all functions available on said motion video transformation system.

16. A motion video transformation system for communication with a diagnostic imaging system, said motion video transformation system comprising:

a computer;

a mass storage device in communication with said computer;

a video processor in communication with said computer;
said video processor comprising:
  a video processor input;
  a video transformation processor in communication with said computer;
  said video processor input for receiving a video signal input from the diagnostic imaging system;
  said video processor for converting said video signal input into video data for processing by said computer;
  said video transformation processor for compressing said video data and providing a compressed video data to said computer;
  a physiological signal acquisition circuit in communication with said computer for receiving physiological signals from a patient and converting said physiological signals into physiological data for processing by said computer;
  said computer being programmed for combining and synchronizing in real-time said compressed video data with said physiological data into compressed indexed video data, said physiological data for providing a reference index in said compressed video data via computer synchronization by correlating an event in said compressed video data to a corresponding event in said physiological signals;
  said computer being programmed for storing said compressed indexed video data to said mass storage device;
  a display monitor in communication with said computer;
  said computer being programmed for displaying a visual catalog on said display monitor and having means for displaying a plurality of video sequences in a display area of said display monitor;
  said visual catalog comprising at least one video frame representation of video sequences previously stored on said mass storage device, wherein a selection of a specific video frame representation from said visual catalog will display a corresponding video sequence in said display area of said display monitor;
  said video sequences being retrieved from corresponding compressed indexed video data stored in said mass storage device;
  a computer generated display comprising a plurality of control buttons on said display monitor for selecting a predetermined function to be performed upon at least one of said plurality of video sequences in said display area of said display monitor,
  said computer being programmed for processing at least one of said plurality of video sequences according to said predetermined function upon selection of a corresponding control button;
  a video display processor;
  said video display processor in communication with said video processor;
  said display monitor in communication with said video display processor,
  said computer being programmed for responding to the selection of a real-time control button from said plurality of control buttons on said display monitor by sending a real-time compressed indexed video data from said computer to said video transformation processor;
  said video transformation processor for decompressing said compressed indexed video data, and providing uncompressed indexed video data to said video display processor; and
  said video display processor for computing an appropriate display format for displaying said uncompressed indexed video data at a predetermined resolution on said display monitor, said video display processor for displaying a real-time video sequence in real-time during acquisition of said video input from the diagnostic imaging system.

17. A motion video transformation system for communication with a diagnostic imaging system, said motion video transformation system comprising:
  a computer;
  a mass storage device in communication with said computer;
  a video processor in communication with said computer;
  said video processor comprising:
    a video processor input;
    a video transformation processor in communication with said computer;
    said video processor input for receiving a video signal input from the diagnostic imaging system;
    said video processor converting said video signal input into video data for processing by said computer;
    said video transformation processor for compressing said video data and providing a compressed video data to said computer;
    a physiological signal acquisition circuit in communication with said computer for receiving physiological signals from a patient and converting said physiological signals into physiological data for processing by said computer;
    said video transformation processor for compressing said video data and providing a compressed video data to said computer;
    a physiological signal acquisition circuit in communication with said computer for receiving physiological signals from a patient and converting said physiological signals into physiological data for processing by said computer;
    said computer being programmed for combining and synchronizing in real-time said compressed video data with said physiological data into compressed indexed video data, said physiological data for providing a reference index in said compressed video data via computer synchronization by correlating an event in said compressed video data to a corresponding event in said physiological signals;
    said computer being programmed for storing said compressed indexed video data to said mass storage device;
    a display monitor in communication with said computer;
    said computer being programmed for displaying a visual catalog on said display monitor and having means for displaying a plurality of video sequences in a display area of said display monitor;
    said visual catalog comprising at least one video frame representation of video sequences previously stored on said mass storage device, wherein a selection of a specific video frame representation from said visual catalog will display a corresponding video sequence in said display area of said display monitor;
    said video sequences being retrieved from corresponding compressed indexed video data stored in said mass storage device;
    a computer generated display comprising a plurality of control buttons on said display monitor for selecting a predetermined function to be performed upon one or more of said plurality of video sequences in said display area of said display monitor;

said video sequences being retrieved from corresponding compressed indexed video data stored in said mass storage device;

a computer generated display comprising a plurality of control buttons on said display monitor for selecting a predetermined function to be performed upon one or more of said plurality of video sequences in said display area of said display monitor;

said computer being programmed for processing at least one of said plurality of video sequences according to said predetermined function upon selection of a corresponding control button;

video display processor;

said video display processor in communication with said video processor, said display monitor in communication with said video display processor;

said computer being programmed for responding to selection of a playback command by retrieving corresponding pre-recorded compressed indexed video data from said mass storage device corresponding to said video sequences which have been selected and providing said compressed indexed video data which corresponds to said video sequences to said video transformation processor;

said video transformation processor for decompressing said compressed indexed video data, and providing uncompressed indexed video data to said video display processor; and said video display processor for computing an appropriate display format for displaying said uncompressed indexed video at a predetermined resolution in said display area of said display monitor.

18. A motion video transformation system with a diagnostic imaging system having means for embedding attribute data into video data, said motion video transformation system comprising:

a computer;

a mass storage device in communication with said computer;

a video processor in communication with said computer;

said video processor comprising
  a video processor input;
  a video transformation processor in communication with said computer;

said video processor input for receiving a video signal input from the diagnostic imaging system;

said video processor for converting said video signal input into video data for processing by said computer;

said video transformation processor for compressing said video data and providing a compressed video data to said computer;

a physiological signal acquisition circuit in communication with said computer for receiving physiological signals from a patient and converting said physiological signals into physiological data for processing by said computer;

said computer being programmed for combining and synchronizing in real-time said compressed video data with said physiological data into compressed indexed video data, said physiological data for providing a reference index in said compressed indexed video data, said physiological data for providing a reference index in said compressed video data via computer synchronization by correlating an event in said compressed video data to a corresponding event in said physiological signals;

said computer being programmed for storing said compressed indexed video data to said mass storage device;

a display monitor in communication with said computer;

said computer being programmed for displaying a visual catalog on said display monitor and having means for displaying a plurality of video sequences in a display area of said display monitor;

said visual catalog comprising at least one video frame representation of video sequences previously stored on said mass storage device, wherein a selection of a specific video frame representation from said visual catalog will display a corresponding video sequence in said display area of said display monitor;

said video sequences being retrieved from corresponding compressed indexed video data stored in said mass storage device;

said computer having means for receiving attribute data embedded into said video data; and said computer being programmed for processing said attribute data for databasing and indexing of said compressed indexed video data stored on said mass storage device.

* * * * *

UNITED STATES PATENT AND TRADEMARK OFFICE
CERTIFICATE OF CORRECTION

PATENT NO. : 5,619,995

DATED : April 15, 1997

INVENTOR(S) : Suave M. Lobodzinski

It is certified that error appears in the above-indentified patent and that said Letters Patent is hereby corrected as shown below:

In column 3, line 64, delete "xmilliseconds" and insert therefor --33 milliseconds--.

Signed and Sealed this

Twenty-fourth Day of March, 1998

Attest:

BRUCE LEHMAN

*Attesting Officer*            *Commissioner of Patents and Trademarks*